(12) United States Patent
Labbe et al.

(10) Patent No.: US 8,211,106 B2
(45) Date of Patent: Jul. 3, 2012

(54) EXTERNAL BONE DISTRACTOR

(75) Inventors: Daniel Labbe, Caen (FR); Jean-Michel Roisin, Draveil (FR); Pierro Sabin, Rouen (FR)

(73) Assignee: OBL, Chatillon (FR)

( * ) Notice: Subject to any disclaimer, the term of this patent is extended or adjusted under 35 U.S.C. 154(b) by 0 days.

(21) Appl. No.: 10/489,597

(22) PCT Filed: Sep. 16, 2002

(86) PCT No.: PCT/FR02/03156
§ 371 (c)(1),
(2), (4) Date: Oct. 4, 2004

(87) PCT Pub. No.: WO03/024341
PCT Pub. Date: Mar. 27, 2003

(65) Prior Publication Data
US 2005/0043731 A1 Feb. 24, 2005

(30) Foreign Application Priority Data
Sep. 14, 2001 (FR) ..................................... 01 11944

(51) Int. Cl.
*A61B 17/58* (2006.01)
(52) U.S. Cl. ........................................................ 606/57
(58) Field of Classification Search .................... 606/53, 606/57–59, 90, 105, 54, 60, 261; 600/209, 600/229–30
See application file for complete search history.

(56) References Cited

U.S. PATENT DOCUMENTS

| | | | | |
|---|---|---|---|---|
| 660,194 | A * | 10/1900 | Lukens | 433/12 |
| 2,372,866 | A * | 4/1945 | Tofflemire | 606/54 |
| 4,365,624 | A * | 12/1982 | Jaquet | 606/56 |
| 4,607,625 | A * | 8/1986 | Schenck | 606/55 |
| 4,773,402 | A * | 9/1988 | Asher et al. | 606/61 |
| 4,790,303 | A * | 12/1988 | Steffee | 606/61 |
| 4,848,368 | A | 7/1989 | Kronner | |
| 4,978,348 | A | 12/1990 | Ilizarov | |
| 5,095,919 | A * | 3/1992 | Monticelli et al. | 606/56 |
| 5,176,679 | A * | 1/1993 | Lin | 606/272 |
| 5,196,016 | A * | 3/1993 | Buser et al. | 606/72 |
| 5,382,248 | A * | 1/1995 | Jacobson et al. | 606/60 |
| 5,403,316 | A * | 4/1995 | Ashman | 606/61 |
| 5,472,407 | A * | 12/1995 | Schenck | 601/40 |
| 5,496,319 | A * | 3/1996 | Allard et al. | 606/56 |
| 5,797,908 | A * | 8/1998 | Meyers et al. | 606/54 |
| 7,422,593 | B2 * | 9/2008 | Cresina et al. | 606/54 |

FOREIGN PATENT DOCUMENTS

| | | | | |
|---|---|---|---|---|
| DE | 19503609 | * | 8/1995 | 606/57 |
| FR | 2671479 | | 7/1992 | |
| JP | 9215699 | * | 8/1997 | 606/57 |

\* cited by examiner

*Primary Examiner* — Eduardo C Robert
*Assistant Examiner* — Tara Carter
(74) *Attorney, Agent, or Firm* — William H. Holt

(57) ABSTRACT

An external bone distractor (1) having a threaded curvilinear rod (4) including several diametrical flat sections (7,8) with the thread (9) of the rod (4) continuing along longitudinal lines. At least a pair of carriages (2) are engaged on the rod and solidly connected to spindle supports (3). Guide members (10, 13) cooperate with the flat sections for preventing rotation of each of the carriages about the axis of the rod. Adjusting devices (14, 15) position each of the carriages along the length of the rod. The curvilinear rod (4) provides for use of the distractor in reconstruction of curved bone segments, such as in the jaw, face and skull.

10 Claims, 3 Drawing Sheets

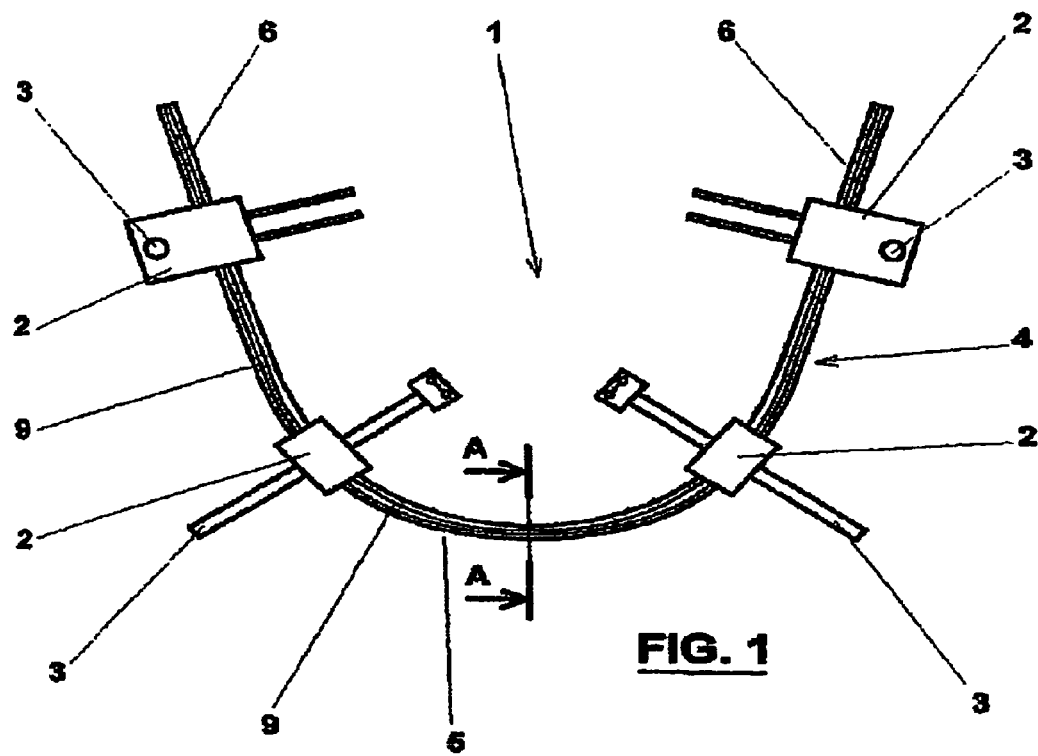
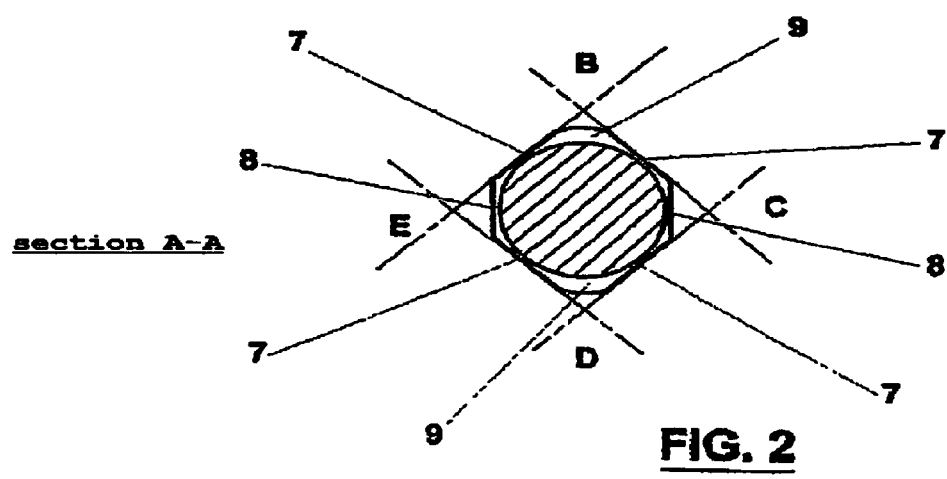

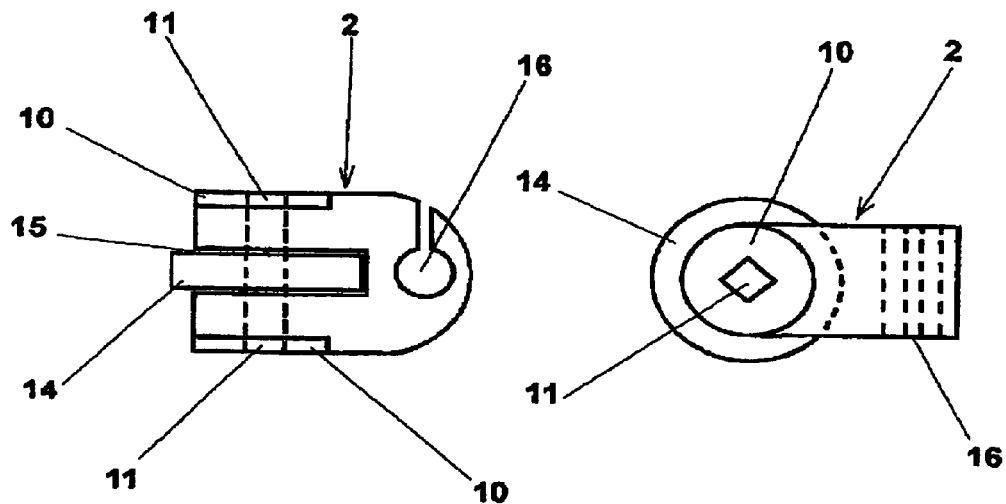
FIG. 5a  FIG. 5b
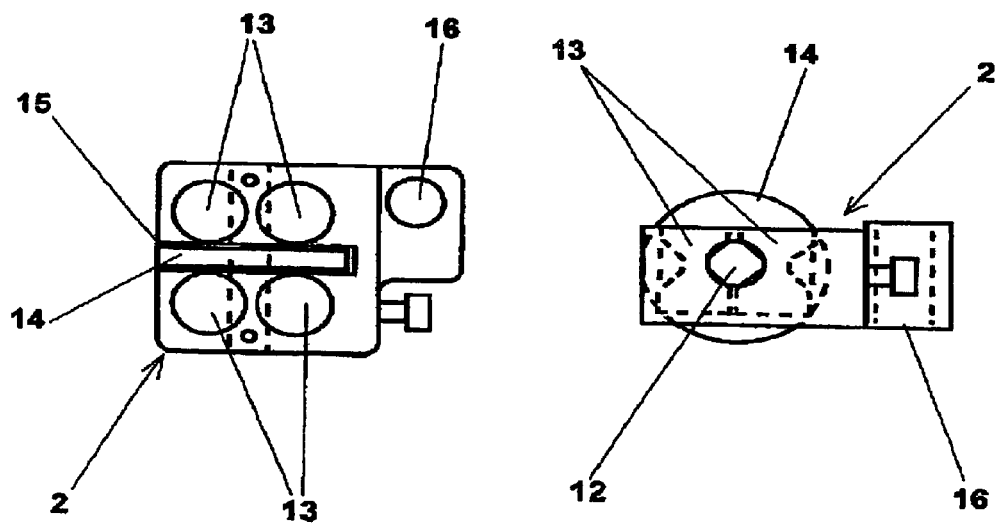
FIG. 6a  FIG. 6b

EXTERNAL BONE DISTRACTOR

TECHNOLOGICAL BACKGROUND TO THE INVENTION

The replacement of a missing bone fragment following resection of a tumour or major trauma often uses operating techniques designed to promote the growth or development of the adjacent healthy section of bone tissue.

One of these comprises exerting tension on the bone callus resulting from an osteotomy in order to lengthen it by an amount corresponding to the bone loss.

This technique, which has been considerably developed by the Russian practitioner Ilizarov, was initially used for the long bones or at least for bone fragments of generally cylindrical shape.

The external distractor described by this author in U.S. Pat. No. 4,978,348 published on 18 Dec. 1990 appears to offer sufficient flexibility of use to enable it to be used both for restoring the shape of the hand, by stretching the parts of phalanges remaining after amputation, and for the reconstruction of the mandible, for example.

The system comprises a set of threaded rods which may be assembled to fit the shape of the bone or set of bones being treated. The threaded rods carry pin-supporting carriages the adjustable spacings of which allow the bone distraction to take place. The pins of each carriage are tightened by a nut between washers threaded onto a hollow bolt engaging on one of the rods. The latter have a flat section cooperating with gudgeons of the hollow bolts for securing the pin supports against rotation relative to the rods.

The apparatus is simple but, as the carriages are held in place on the rods by locknuts, two spanners are needed to move them. Moreover, the locking and unlocking of a locknut requires a relatively complex simultaneous manipulation of these two spanners.

The external osteosynthesis fixator disclosed in Utility Certificate Application FR 2,671,479 in the name of the company Hit Medica, published on 17 Jul. 1992, is based on the principle of the turnbuckle. The two spindle supports are thus simply moved apart by manipulating the central part of the rod, the ends of which are threaded in opposite directions.

Based on another principle, the apparatus described in U.S. Pat. No. 4,848,368 published on 18 Jul. 1989 in the name of R. Kronner can according to the applicant be manoeuvred using a single knurled wheel. In this case the patient himself can perform the task.

The two systems mentioned above may be used for the distraction of straight bones, be they long or short, but they are not suitable for curved bones such as, for example, the bones of the skull, the mandibles or the ribs.

An apparatus which is specially adapted for the curved bone segments of jaws, face or cranium is described in German Patent Application DE 195 03 609 published on 10 Aug. 1995 in the name of Messrs Normed Medizin Technik Vertriebs. The apparatus is formed from a plurality of racks on which pin-supporting carriages are fixed. The racks are articulated to one another so that the assembly fits the shape of the bone on the outside. A carriage can be moved along a rack using a screw engaging therewith.

The joints between the racks comprise spherical connections, which has the advantage of allowing the assembly to be made in any shape. However, these joints have the serious disadvantage of restricting the movement of the carriages.

A threaded, curved, continuous rail which does not limit the movement of the pin-supporting carriages is disclosed in Japanese Patent Application JP 09-215699 published on 19 Aug. 1997 in the name of Messrs Nagoya Rashi Seisakusho.

According to the embodiment shown in the Figures accompanying the application, the rail has a square cross section and is threaded on each of its edges. In the example of use described, the rail is fixed to the right-hand side of a mandible and follows the contour thereof, from back to front, without going past the start of the chin.

However, it appears technically impossible for the rail described in JP application 09-215699 to follow the contour of the mandible beyond the start of the chin. The small radius of curvature at the chin would obviously result in a substantial deformation of the threads of the rod and prevent the rotation of the nuts which control the movement of the carriages.

In fact, in the position shown in the drawings which accompany JP application 09-215699, the threads inside the curve followed by the rod are necessarily compressed, while the outer threads are moved apart.

As a result, the curved rail would appear to be usable only for repairing a side part of the mandible, as shown in the main Figure, and certainly not for distraction of the median part of the mandible.

Consequently, it is apparent from the prior art as described in the documents cited above that external bone distractors adapted for the reconstruction of curved bone segments, notably the bones of the jaw, face and cranium, are known, but at present there is no osteogenic distraction device which has features that fully meet the needs of maxillo-facial surgery.

GENERAL DESCRIPTION OF THE INVENTION

The present invention therefore relates to an external bone distractor comprising in known manner:
- a threaded curvilinear rod comprising a plurality of diametrically opposed flat sections, preserving the threading of the rod along longitudinal bands,
- at least two carriages engaging on said rod and solidly attached to pin supports,
- guide means which co-operate with said flat sections in order to prevent the rotation of each of the carriages around the axis of the rod,
- means for adjusting the position of each of the carriages along the rod.

The invention specifically relates to a distractor of this type the essential feature of which is that the longitudinal bands along which the threads are preserved extend solely in the vicinity of the neutral fibres of the rod.

According to an additional feature of the distractor according to the invention there are only two of these longitudinal bands and they are diametrically opposed.

Preferably, the rod, more simply, forms a curved plane.

Advantageously the curve formed substantially fits the shape of the mandible. It is preferably made up of a 150° arc of a circle, the ends of which are extended by two straight segments.

In one particular embodiment of the distractor, the threaded rod has six diametrically opposed flat sections machined so that the sides of the straight section of the rod, and their extensions, adjacent to the lines of the neutral fibres, form a square.

Preferably, the guide means comprise at least one washer solidly attached to each of the carriages engaging on the rod by means of an axial bore the section of which is complementary to the cross section of said rod.

According to an alternative embodiment of the external bone distractor according to the invention these guide means comprise at least one pair of dual wheels the rotation axles of which are firmly attached to those of the carriages, arranged to straddle the rod on either side and rolling on said rod.

As for the adjustment means, these preferably comprise a knurled nut screwed onto the rod acting on each of the carriages by means of a bracket.

Advantageously the guide means for a carriage have two positions: the direction of the pin support in one of the positions is perpendicular to the direction of the pin support in the other position.

There is an advantage in the fact that at least two of the carriages of the external bone distractor according to the invention are fixed and that a third is movable along the rod.

BRIEF DESCRIPTION OF THE DRAWINGS

FIGS. 1, 3 and 4 diagrammatically show the bone distractor according to the invention viewed from below, from in front and from the left, respectively.

FIG. 2 shows an enlarged cross section through the threaded rod which forms part of the distractor according to a preferred embodiment of the invention.

FIGS. 5a and 5b show a first embodiment of one of the pin-supporting carriages of the distractor according to the invention viewed from above and from the front, respectively.

FIGS. 6a and 6b show an alternative embodiment of one of the pin-supporting carriages of the distractor according to the invention, with the cover removed, viewed from above and from the front, respectively.

Figure 3:
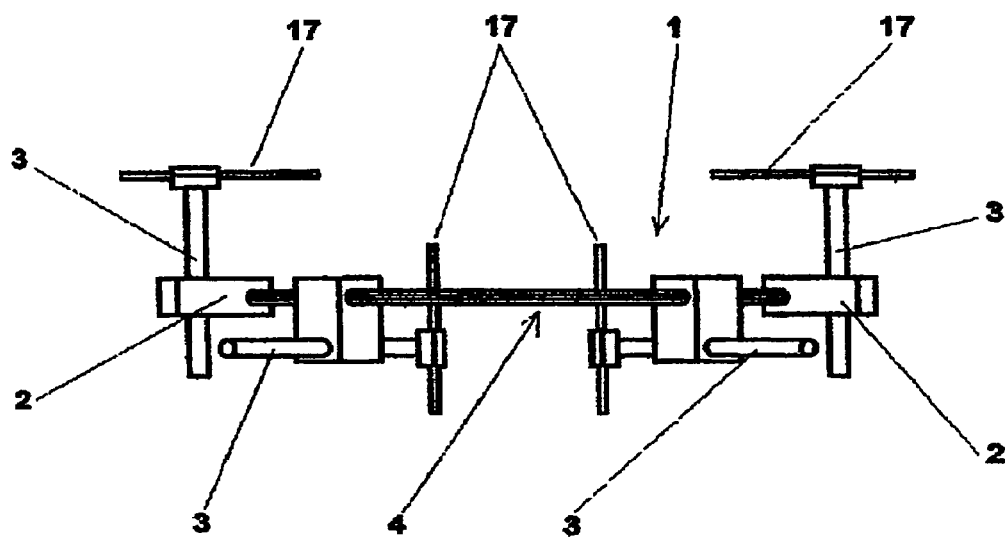

DESCRIPTION OF THE PREFERRED
EMBODIMENTS OF THE INVENTION

The references to FIG. 1 and FIG. 2 will serve to explain the general principle of the invention by describing a model apparatus adapted to jaw reconstruction by progressive bone distraction.

FIG. 1 is a simplified view of the distractor 1 from below. Carriages 2 are shown, supporting pin supports 3 engaging on a threaded rod 4.

Unlike known devices comprising one or more straight rods, this threaded rod 4 is continuous and its shape substantially fits the outer shape of the jaw.

It has a front section 5 in the shape of a 150° arc of a circle with a radius of 70 mm, and two side sections 6 consisting of straight segments 90 mm long.

FIG. 2 clearly shows in section (section AA) the other essential feature of the threaded rod 4. Six flat sections 7,8 formed in a threaded rod to ISO standard M6 preserve the threading 9 only in the vicinity of the neutral fibres of the rod 4, i.e. the fibres of the rod 4 which are not subjected to extension or compression and which are therefore located in the vicinity of each of the two planes at a tangent to the rod 4 which are parallel to the plane in which said rod extends. Each preserved part 9 of the thread thus retains the nominal characteristics of the profile of the threads and of the pitch of the threaded rod 4 and can consequently co-operate with a nut of the corresponding size. This nut, as will be explained in connection with FIGS. 5 and 6, will constitute a means of adjusting the position of a carriage 2 along the rod 4.

Figure 4:
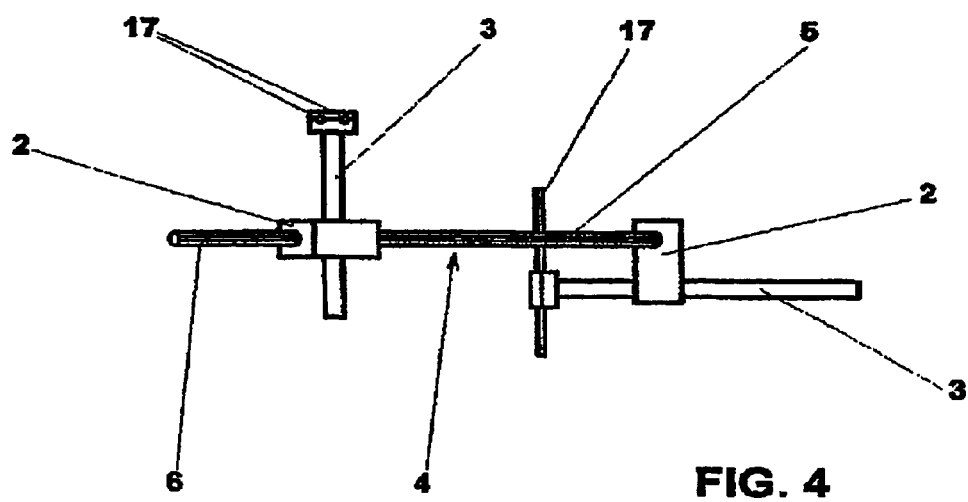

As shown in FIGS. 3 and 4, the carriages 2 are capable of holding the pin supports 3 either in a position which is perpendicular to the plane of the distractor 1 (carriages 2 on the front section 5), or in a parallel position (carriages 2 on the side sections 6).

To do this, the carriages 2 are guided on the rod 4 and secured against rotation thereon by guide means adapted to the particular shape of the section (FIG. 2) of the threaded rod 4.

The sides 7 of this straight section adjacent to the preserved parts 9 of the thread in the vicinity of the neutral fibres, and the extensions thereof, in fact form a square BCDE.

In a first preferred embodiment of the distractor 1, a carriage 2 is integral with two aligned washers 10 the axial bore 11 of which is square in section, as is clearly shown in FIG. 5b, i.e. complementary to the rod 4 on which they are engaged. The carriage 2 can therefore slide along the threaded rod 4 but has only two positions of axial rotation, at 90° to one another, depending on the manner in which it has been threaded on the rod 4.

According to an alternative embodiment shown in FIGS. 6a and 6b, the channel 12 of square section in which the threaded rod 4 travels inside a carriage 2 is obtained by means of two pairs of aligned dual wheels 13. The dual wheels 13 rotate in four cylindrical recesses in the body that constitutes the carriage 2, thus allowing the threaded rod 4 to slide while being guided.

The carriage is shown with the "cover removed", so as to allow these dual wheels 13 to be seen in FIG. 6a.

As before, the carriage 2 may be oriented on the rod in two different ways.

The free space left in the body of the carriage 2, between the washers 10 or the dual wheels 13, for accommodating a knurled nut 14 screwed onto the rod 4, forms a bracket 15 which transmits the movements of this nut 14 to the carriage 2.

The nut can easily be manipulated by the patient himself. A ratchet indicates the number of fractions of a turn made.

Cylindrical bores 16 are provided in the body of the carriages for receiving the rods of the pin supports 3, which are immobilised by screws.

These very lightweight and very simple structures of the carriages 2, according to the views of the distractor 1 according to the invention shown in FIGS. 1, 3 and 4, therefore enable the pins 17 to be placed ideally at the most favourable points on the jaw to produce the desired bone distraction without any problems.

The travel profile of the carriages 2, ideally suited to the shape of the jaw, makes the distraction particularly progressive.

It will be appreciated that the rod 4 acting as a rail must be kept firmly attached to the jaw by the pins of at least two fixed carriages 2. At least a third carriage is movable to allow the movement of the bone.

The advantages of the curved shape of the threaded rod 4 are easily transposed to cases other than the jaw; a rod of suitable size and shape for the skull would constitute the basis of an apparatus for distracting the cranium.

It goes without saying that the invention is not limited to just the technical specifications described above by way of example; on the contrary it includes all the other possible alternative embodiments.

In particular, the guide means 10, 13 for the carriages 2 or the means for regulating their positions 14 described above are not restrictive. Any other mechanical means used for the same purposes constitute a possible variant which does not go beyond the inventive concept of the external bone distractor the features of which are specified below.

The invention claimed is:
1. An external bone distractor (1) comprising:
a curvilinear rod (4) comprising a plurality of diametrically opposed flat sections (7, 8),
at least two carriages (2) engaging on said rod (4) and solidly attached to pin supports (3), guide means (10, 13) which co-operate with said flat sections (7, 8) for preventing rotation of each of said carriages (2) around the axis, of said rod (4), means (14, 15) for adjusting the position of each of said carriages (2) along said rod (4), characterised in that said curvilinear rod is provided with threading (9) extending solely on upper and lower surfaces of said rod along neutral fibres extending along longitudinal bands located on upper and lower surfaces of said rod, and said bands extend solely in the vicinity of said neutral fibres of said rod (4).

2. An external bone distractor (1) according to claim 1, wherein there are only two longitudinal bands having threading (9) and said bands are diametrically opposed.

3. An external bone distractor (1) according to claim 2, wherein the rod (4) forms a flat curve.

4. An external bone distractor (1) according to claim 3, wherein said rod (4) forms a curve configured to substantially fit the shape of a patient's jaw on the outside, the ends of which are extended by two straight segments (6).

5. An external bone distractor (1) according to claim 1, wherein the guide means (10, 13) comprise at least one washer (10) solidly attached to each of the carriages (2), engaging on the rod (4) by means of an axial bore (11) of complementary section to said flat sections (7, 8) of said rod (4).

6. An external bone distractor (1) according to claim 1, wherein the adjusting means (14, 15) comprise a knurled nut (14) screwed onto the rod (4) acting on each of the carriages (2) via a bracket (15).

7. An external bone distractor (1) according to claim 1, wherein each of the guide means (10, 13) has two positions, the direction of the pin support (3) in one of said positions being perpendicular to the direction of the pin support (3) in the other said position.

8. An external bone distractor (1) according to claim 1, wherein at least two of said carriages (2) are fixed, and at least a third is movable along the rod (4).

9. An external bone distractor (1) comprising:

a curvilinear rod (4) comprising a plurality of diametrically opposed flat sections (7, 8), said rod being provided with threading solely on upper and lower surfaces thereof, the threading (9) of the rod (4) being preserved along neutral fibres extending along longitudinal bands located on said upper and lower surfaces of said rod, at least two-carriages (2) engaging on said rod (4) and solidly attached to pin supports (3), guide means (10, 13) which co-operate with said flat sections (7, 8) for preventing rotation of each of said carriages (2) around the axis of said rod (4), means (14, 15) for adjusting the position of each of said carriages (2) along said rod (4), characterised in that said bands extend solely in the vicinity of said neutral fibres of said rod (4); wherein there are only two bands (9) and they are diametrically opposed, said rod (4) forming a flat curve configured to substantially fit the shape of a patient's jaw on the outside, the ends of which are extended by two straight segments (6), and said rod (4) has six diametrically opposed flat sections (7, 8) machined so that the sides of said straight segments of said rod (4), and their extensions, adjacent to the lines of the neutral fibres (9), form a square (BCDE).

10. An external bone distractor (1) according to claim 9, wherein said guide means (10, 13) comprise at least one pair of dual wheels (13) the rotation axles of which are integral with those of the carriages (2), and arranged to straddle said rod (4) on either side, for rolling thereon.

\* \* \* \* \*